(12) United States Patent
Pu et al.

(10) Patent No.: US 7,819,816 B2
(45) Date of Patent: Oct. 26, 2010

(54) PERIODIC DISORDERED BREATHING DETECTION

(75) Inventors: Yanchuan Pu, Minneapolis, MN (US); Kent Lee, Shoreview, MN (US); Jonathan Kwok, Shoreview, MN (US); Zheng Lin, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 818 days.

(21) Appl. No.: 11/392,365

(22) Filed: Mar. 29, 2006

(65) Prior Publication Data

US 2007/0239057 A1 Oct. 11, 2007

(51) Int. Cl.
*A61B 5/08* (2006.01)
*A61B 5/02* (2006.01)
*A61N 1/00* (2006.01)

(52) U.S. Cl. .................. 600/529; 600/484; 600/508

(58) Field of Classification Search ................. 600/345, 600/347, 365, 484, 508, 529; 204/403.01
See application file for complete search history.

(56) References Cited

U.S. PATENT DOCUMENTS 4,562,841 A 1/1986 Brockway et al.

(Continued)

FOREIGN PATENT DOCUMENTS

EP 1151719 7/2001

(Continued)

OTHER PUBLICATIONS

U.S. Appl. No. 11/291,525, filed Dec. 1, 2005, Kwok et al.

(Continued)

*Primary Examiner*—Patricia C Mallari
(74) *Attorney, Agent, or Firm*—Hollingsworth & Funk, LLC

(57) ABSTRACT

Systems and methods are directed to evaluating breathing disorders, such as periodic disordered breathing. A signal representative of patient respiration is developed, typically patient-internally. An envelope of the signal is provided. Periodicity of the envelope is detected, and presence and severity of periodic disordered breathing is determined based on the periodicity of the envelope.

24 Claims, 10 Drawing Sheets

U.S. PATENT DOCUMENTS

| | | | |
|---|---|---|---|
| 4,697,591 A * | 10/1987 | Lekholm et al. | 607/20 |
| 4,928,688 A | 5/1990 | Mower | |
| 5,036,849 A | 8/1991 | Hauck et al. | |
| 5,063,927 A | 11/1991 | Webb et al. | |
| 5,133,353 A | 7/1992 | Hauser | |
| 5,179,945 A | 1/1993 | Van Hofwegen et al. | |
| 5,203,348 A | 4/1993 | Dahl et al. | |
| 5,230,337 A | 7/1993 | Dahl et al. | |
| 5,284,136 A | 2/1994 | Hauck et al. | |
| 5,301,677 A | 4/1994 | Hsung | |
| 5,314,459 A | 5/1994 | Swanson et al. | |
| 5,318,597 A | 6/1994 | Hauck et al. | |
| 5,334,222 A | 8/1994 | Salo et al. | |
| 5,360,442 A | 11/1994 | Dahl et al. | |
| 5,366,496 A | 11/1994 | Dahl et al. | |
| 5,372,606 A | 12/1994 | Lang et al. | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,411,525 A | 5/1995 | Swanson et al. | |
| 5,468,254 A | 11/1995 | Hahn et al. | |
| 5,540,727 A | 7/1996 | Tockman et al. | |
| 5,545,202 A | 8/1996 | Dahl et al. | |
| 5,593,431 A | 1/1997 | Sheldon | |
| 5,603,732 A | 2/1997 | Dahl et al. | |
| 5,620,466 A | 4/1997 | Haefner et al. | |
| 5,634,938 A | 6/1997 | Swanson et al. | |
| 5,662,688 A | 9/1997 | Haefner et al. | |
| 5,697,953 A | 12/1997 | Kroll et al. | |
| 5,836,987 A | 11/1998 | Baumann et al. | |
| 5,916,243 A | 6/1999 | KenKnight et al. | |
| 5,957,861 A | 9/1999 | Combs et al. | |
| 5,974,340 A * | 10/1999 | Kadhiresan | 607/18 |
| 5,974,349 A | 10/1999 | Levine | |
| 6,026,320 A | 2/2000 | Carlson et al. | |
| 6,044,297 A | 3/2000 | Sheldon et al. | |
| 6,044,298 A | 3/2000 | Salo et al. | |
| 6,055,454 A | 4/2000 | Heemels | |
| 6,221,011 B1 | 4/2001 | Bardy | |
| 6,270,457 B1 | 8/2001 | Bardy | |
| 6,275,727 B1 | 8/2001 | Hopper et al. | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,358,203 B2 | 3/2002 | Bardy | |
| 6,360,127 B1 | 3/2002 | Ding et al. | |
| 6,368,284 B1 | 4/2002 | Bardy | |
| 6,371,922 B1 | 4/2002 | Baumann et al. | |
| 6,398,728 B1 | 6/2002 | Bardy | |
| 6,409,675 B1 | 6/2002 | Turcott | |
| 6,411,848 B2 | 6/2002 | Kramer et al. | |
| 6,424,865 B1 | 7/2002 | Ding | |
| 6,438,407 B1 | 8/2002 | Ousdigian et al. | |
| 6,438,410 B2 | 8/2002 | Hsu et al. | |
| 6,440,066 B1 | 8/2002 | Bardy | |
| 6,449,509 B1 | 9/2002 | Park et al. | |
| 6,454,719 B1 | 9/2002 | Greenhut | |
| 6,459,929 B1 | 10/2002 | Hopper et al. | |
| 6,480,733 B1 | 11/2002 | Turcott | |
| 6,513,532 B2 | 2/2003 | Mault et al. | |
| 6,527,729 B1 | 3/2003 | Turcott | |
| 6,542,775 B2 | 4/2003 | Ding et al. | |
| 6,564,106 B2 | 5/2003 | Guck et al. | |
| 6,572,557 B2 | 6/2003 | Tchou et al. | |
| 6,589,188 B1 | 7/2003 | Street et al. | |
| 6,597,951 B2 | 7/2003 | Kadhiresan et al. | |
| 6,600,949 B1 | 7/2003 | Turcott | |
| 6,641,542 B2 | 11/2003 | Cho et al. | |
| 6,658,292 B2 | 12/2003 | Kroll et al. | |
| 6,666,826 B2 | 12/2003 | Salo et al. | |
| 6,705,990 B1 | 3/2004 | Gallant et al. | |
| 6,708,058 B2 | 3/2004 | Kim et al. | |
| 6,741,885 B1 | 5/2004 | Bornzin et al. | |
| 6,752,765 B1 | 6/2004 | Strobel et al. | |
| 6,773,404 B2 | 8/2004 | Poezevera et al. | |
| 6,830,548 B2 | 12/2004 | Bonnet et al. | |
| 6,832,113 B2 | 12/2004 | Belalcazar | |
| 6,856,829 B2 * | 2/2005 | Ohsaki et al. | 600/479 |
| 6,922,587 B2 | 7/2005 | Weinberg | |
| 6,993,389 B2 | 1/2006 | Ding | |
| 7,013,176 B2 | 3/2006 | Ding | |
| 7,020,521 B1 | 3/2006 | Brewer et al. | |
| 7,041,061 B2 | 5/2006 | Kramer | |
| 7,113,823 B2 | 9/2006 | Yonce et al. | |
| 7,115,096 B2 | 10/2006 | Siejko | |
| 7,127,290 B2 | 10/2006 | Girouard | |
| 7,158,830 B2 | 1/2007 | Yu | |
| 7,181,285 B2 | 2/2007 | Lindh | |
| 7,206,634 B2 | 4/2007 | Ding et al. | |
| 7,228,174 B2 | 6/2007 | Burnes | |
| 7,306,564 B2 | 12/2007 | Nakatani et al. | |
| 7,310,554 B2 | 12/2007 | Kramer | |
| 7,343,199 B2 | 3/2008 | Hatlestad | |
| 7,376,457 B2 | 5/2008 | Ross | |
| 7,389,141 B2 | 6/2008 | Hall | |
| 7,409,244 B2 | 8/2008 | Salo | |
| 7,468,032 B2 | 12/2008 | Stahmann et al. | |
| 7,483,743 B2 | 1/2009 | Mann et al. | |
| 7,572,225 B2 | 8/2009 | Stahmann et al. | |
| 2001/0037067 A1 | 11/2001 | Tchou et al. | |
| 2001/0049470 A1 | 12/2001 | Mault et al. | |
| 2002/0143264 A1 | 10/2002 | Ding et al. | |
| 2002/0193697 A1 | 12/2002 | Cho et al. | |
| 2003/0055461 A1 | 3/2003 | Girouard et al. | |
| 2003/0078619 A1 * | 4/2003 | Bonnet et al. | 607/4 |
| 2004/0019289 A1 * | 1/2004 | Ross | 600/519 |
| 2004/0116819 A1 | 6/2004 | Alt | |
| 2004/0122294 A1 | 6/2004 | Hatlestad et al. | |
| 2004/0127792 A1 | 7/2004 | Siejko | |
| 2004/0133079 A1 | 7/2004 | Mazar et al. | |
| 2005/0085738 A1 | 4/2005 | Stahmann et al. | |
| 2005/0113711 A1 * | 5/2005 | Nakatani et al. | 600/534 |
| 2005/0137629 A1 | 6/2005 | Dyjach et al. | |
| 2007/0055115 A1 | 3/2007 | Kwok et al. | |
| 2007/0073168 A1 | 3/2007 | Zhang et al. | |
| 2007/0118183 A1 | 5/2007 | Gelfand et al. | |
| 2007/0135725 A1 | 6/2007 | Hatlestad | |
| 2007/0179389 A1 | 8/2007 | Wariar | |
| 2008/0262360 A1 | 10/2008 | Dalal et al. | |

FOREIGN PATENT DOCUMENTS

| | | |
|---|---|---|
| EP | 1177764 | 6/2002 |
| WO | WO9833553 | 6/1998 |
| WO | WO0240096 | 5/2002 |
| WO | WO03075744 | 9/2003 |
| WO | WO 2004062485 | 7/2004 |
| WO | WO 2005028029 | 3/2005 |
| WO | WO2008085309 | 7/2008 |

OTHER PUBLICATIONS

P. Solin, T. Roebuck, J. Swieca, E.J. Walters and M. Naughton, Effects of Cardiac Dysfunction on Non-Hypercapnic Central Sleep Apnea, Department of Respiratory Medicine, Alfred Hospital, and Department of Medicine, Monash University Medical School, Melbourne, Victoria, Australia, Apr. 10, 1997, pp. 104-110.

Dark et al., Breathing Pattern Abnormalities and Arterial Oxygen Desaturation During Sleep in the Congestive Heart Failure Syndrome, Chest, Jun. 1987, 6:833-6. Abstract Only.

Hoffman et al., Cheyne-Stokes Respiration in Patients Recovering from Acute Cardiogenic Pulmonary Edema, Chest 1990, 97:410-12. Abstract Only.

Rees et al., Paroxysmal Nocturnal Dyspnoea and Periodic Respiration, The Lancet, Dec. 22-29, 1979, pp. 1315-1317. Abstract Only.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

Butler et al., *Beta-Blocker Use and Outcomes Among Hospitalized Heart Failure Patients*, Journal of the American College of Cardiology, vol. 47, No. 12, 2006, pp. 2462-2469.

Duguet et al., *Expiratory Flow Limitation as a Determinant of Orthopnea in Acute Left Heart Failure*, Journal of the American College of Cardiology, vol. 35, No. 3, 2000, pp. 690-700.

Rame et al., *Outcomes after emergency department discharge with a primary diagnosis of heart failure*, American Heart Journal, vol. 142(4), Oct. 2001, pp. 714-719, Abstract only.

Dimopolou I, et al., *Pattern of Breathing during Progressive Exercise in Chronic Heart Failure*, IJC 81 (2001), 117-121. Abstract Only.

Lee et al., *Predicting Mortality Among Patients Hospitalized for Heart Failure, derivation and validation of a clinical model*. JAMA, 2003, 290:2581-87.

Solin et al., *Effects of Cardiac Dysfunction on Non-Hypercapnic Central Sleep Apnea*, Department of Respiratory Medicine, Alfred Hospital, and Department of Medicine, Monash University Medical School, Melbourne, Victoria, Australia, Apr. 10, 1997, pp. 104-110.

Office Action from U.S. Appl. No. 11/291,525 dated Dec. 8, 2009, 12 pages.

Office Action from U.S. Appl. No. 11/291,525 dated Jun. 24, 2009, 13 pages.

Office Action from U.S. Appl. No. 11/291,525 dated Nov. 28, 2008, 12 pages.

\* cited by examiner

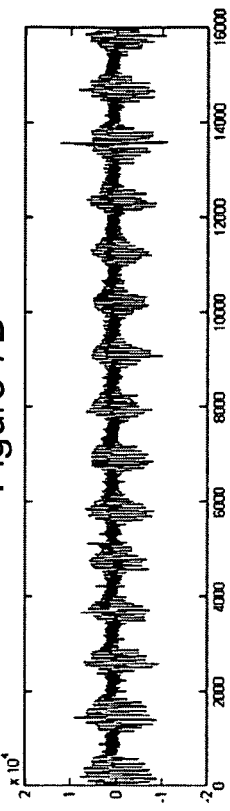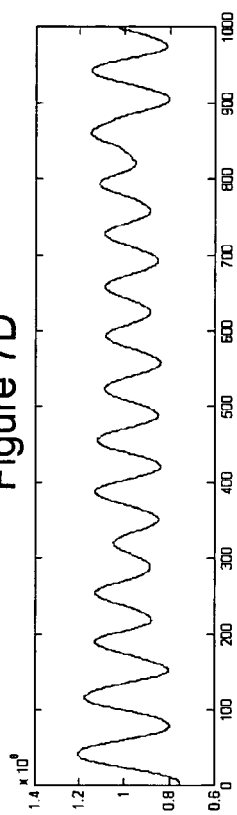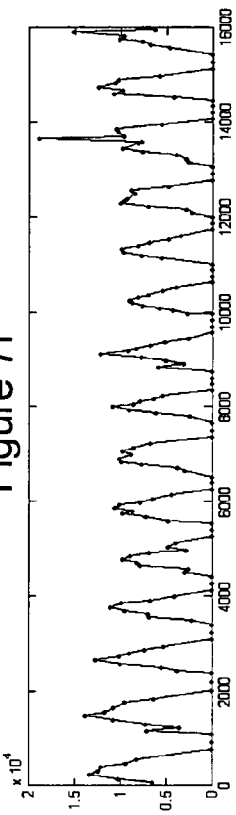
Figure 7B    Figure 7D    Figure 7F
Periodic Breathing
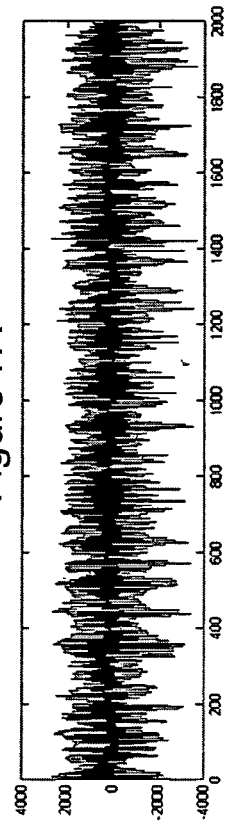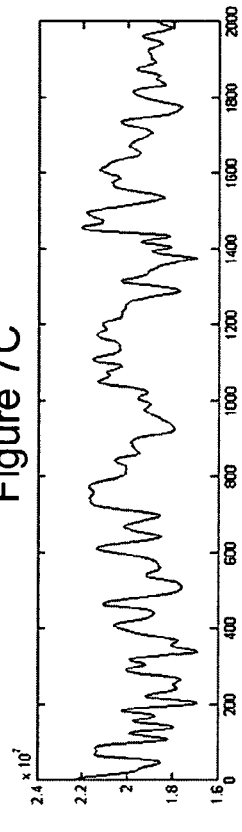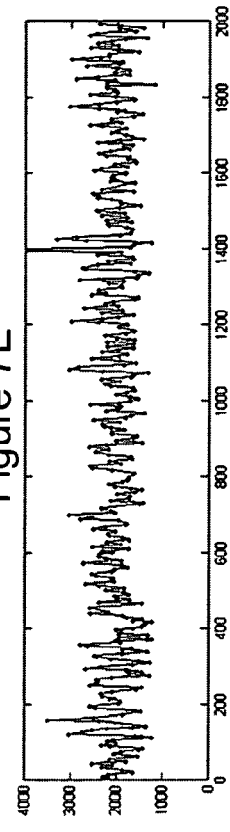
Figure 7A    Figure 7C    Figure 7E
Normal Breathing

PERIODIC DISORDERED BREATHING DETECTION

FIELD OF THE INVENTION

The present invention relates generally to detecting the presence of breathing disorders and, in particular, periodic disordered breathing.

BACKGROUND OF THE INVENTION

Sleep is generally beneficial and restorative to a patient, exerting great influence on the quality of life. The human sleep/wake cycle generally conforms to a circadian rhythm that is regulated by a biological clock. Regular periods of sleep enable the body and mind to rejuvenate and rebuild. The body may perform various tasks during sleep, such as organizing long term memory, integrating new information, and renewing tissue and other body structures.

Lack of sleep and/or decreased sleep quality may have a number of causal factors including, e.g., respiratory disturbances, nerve or muscle disorders, and emotional conditions, such as depression and anxiety. Chronic, long-term sleep-related disorders e.g., chronic insomnia, sleep-disordered breathing, and sleep movement disorders may significantly affect a patient's sleep quality and quality of life.

Sleep apnea, for example, is a fairly common breathing disorder characterized by periods of interrupted breathing experienced during sleep. Sleep apnea is typically classified based on its etiology. One type of sleep apnea, denoted obstructive sleep apnea, occurs when the patient's airway is obstructed by the collapse of soft tissue in the rear of the throat. Central sleep apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and occasionally for a minute or longer.

In addition to apnea, other types of disordered respiration have been identified, including, for example, hypopnea (shallow breathing), dyspnea (labored breathing), hyperpnea (deep breathing), and tachypnea (rapid breathing). Combinations of the disordered respiratory events described above have also been observed. For example, Cheyne-Stokes respiration (CSR) is associated with rhythmic increases and decreases in tidal volume caused by alternating periods of hyperpnea followed by apnea and/or hypopnea. The breathing interruptions of CSR may be associated with central apnea, or may be obstructive in nature. CSR is frequently observed in patients with congestive heart failure (CHF) and is associated with an increased risk of accelerated CHF progression.

An adequate duration and quality of sleep is required to maintain physiological homeostasis. Untreated, sleep disorders may have a number of adverse health and quality of life consequences ranging from high blood pressure and other cardiovascular disorders to cognitive impairment, headaches, degradation of social and work-related activities, and increased risk of automobile and other accidents.

SUMMARY OF THE INVENTION

The present invention is directed to systems and methods for evaluating breathing disorders and, more particularly, to determining the presence of periodic disordered breathing. Embodiments of the invention are directed to methods that involve developing a signal representative of patient respiration and providing an envelope of the signal. Methods further involve detecting periodicity of the envelope, and determining presence of periodic disordered breathing based on the periodicity of the envelope. One, some, or all of these processes may be performed patient-internally, patient-externally, or a combination thereof.

Providing the envelope of the signal may involve removing a trend or DC component of the signal and rectifying the signal. Providing the envelope of the signal may alternatively involve squaring and low pass filtering the signal.

Detecting periodicity of the envelope may involve determining regularity of envelope periodicity. According to one approach, determining regularity of envelope periodicity involves computing a standard deviation ($K_{SD}$) of duration for n envelope cycles occurring within a time window having a predetermined duration. Envelope periodicity may be determined if the standard deviation ($K_{SD}$) is less than a first threshold and n is greater than a second threshold.

Determining presence of periodic disordered breathing may involve determining regularity of envelope periodicity and a duration of envelope cycles occurring within a time window of predetermined duration. Determining presence of periodic disordered breathing may involve computing, within a time window of predetermined duration, a mean ($K_{MEAN}$) indicative of average envelope cycle length and a standard deviation ($K_{SD}$) of the mean ($K_{MEAN}$) computed for n envelope cycles occurring within the time window. Presence of periodic disordered breathing may be determined if the standard deviation ($K_{SD}$) is less than a first threshold, n is greater than a second threshold, and $K_{MEAN}$ falls within a third threshold range.

Methods of the present invention may involve computing a number of periodic disordered breathing events occurring within a time window of predetermined duration by dividing the predetermined duration by a mean ($K_{MEAN}$) indicative of average envelope cycle length. Methods may further involve computing an estimated apnea-hypopnea index based on the number of periodic disordered breathing events occurring within each of a plurality of the time windows, wherein a total duration of the plurality of time windows defines a duration of patient sleep.

Methods of the present invention may involve determining severity of the periodic disordered breathing. For example, determining the severity of the patient's periodic disordered breathing may involve distinguishing between central sleep apnea and obstructive sleep apnea (as well as considering other signals such as blood pressure and oxygen concentration, for example). Determining the severity or progression of congestive heart failure (CHF) may involve determining the presence of periodic disordered breathing in each of a plurality of physiological states, including sleep, wakefulness with exercise, and wakefulness without exercise. Determining the severity of the periodic disordered breathing may also involve determining a frequency of the periodicity and/or a stability of the periodicity. Determining the severity of the periodic disordered breathing may involve determining a depth of a change in peaks of the envelope (e.g., a depth of modulation of the envelope profile or a change of modulation depth).

The signal representative of patient respiration typically comprises a respiratory-modulated physiological signal. For example, the signal representative of patient respiration may be a respiratory-modulated cardiac electrical signal or a respiratory-modulated mechanical signal.

In accordance with other embodiments, systems of the present invention may include a housing and detection circuitry provided in the housing and configured to detect a signal representative of patient respiration. A processor is configured to detect periodicity of an envelope of the signal and determine presence of periodic disordered breathing based on the periodicity of the envelope. In some configurations, the detection circuitry and the processor are disposed in an implantable housing. In other configurations, the detection circuitry is disposed in an implantable housing and the processor is disposed in a patient-external system. In some configurations, the detection circuitry and processor are configured for patient-external implementation.

The processor is configured to detect regularity of envelope periodicity. Typically, the processor is also configured to determining a duration of envelope periodicity. In some configurations, the processor may be configured to compute an estimated apnea-hypopnea index based on the periodicity of the envelope. The processor may also be configured to determine severity of the periodic disordered breathing.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 7A-7D show raw respiration waveforms and envelopes of same for normal and periodic breathing developed in accordance with embodiments of the present invention;

FIGS. 7E-7F show calculated respiration envelopes for normal and periodic breathing based on peak detection of a trans-thoracic impedance signal;

Figure 1:
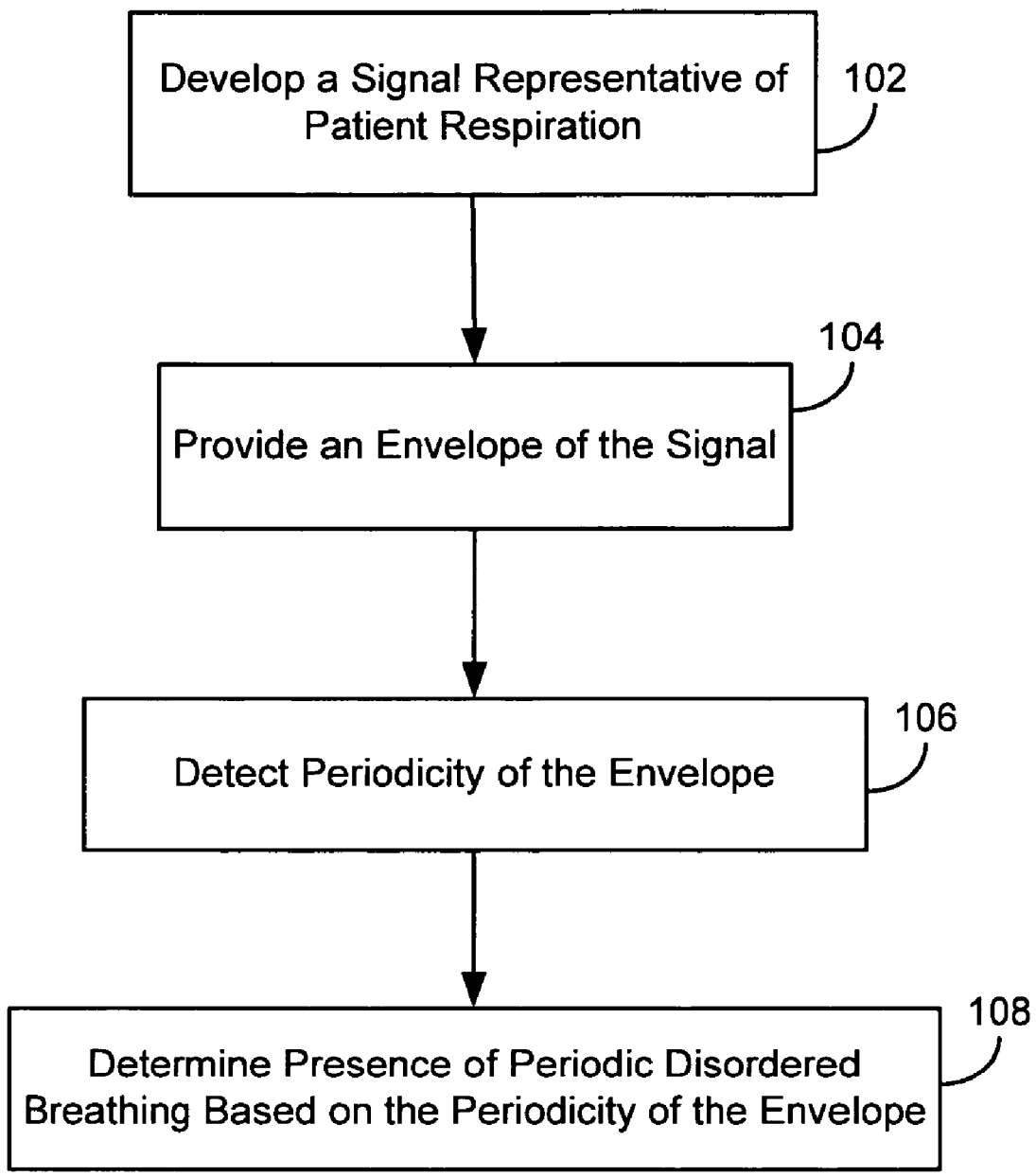
FIG. 1 illustrates a method for detecting the presence of periodic disordered breathing in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the present invention.

An adequate quality and quantity of sleep is required to maintain physiological homeostasis. Prolonged sleep deprivation or periods of highly fragmented sleep ultimately will have serious health consequences. Chronic fragmented sleep may be associated with various cardiac or respiratory disorders affecting a patient's health and quality of life.

By way of example, a significant percentage of patients between 30 and 60 years experience some symptoms of disordered breathing, primarily during periods of sleep. Sleep disordered breathing is associated with excessive daytime sleepiness, systemic hypertension, increased risk of stroke, angina and myocardial infarction. Disturbed respiration can be particularly serious for patients concurrently suffering from cardiovascular deficiencies. Disordered breathing is particularly prevalent among congestive heart failure patients, and may contribute to the progression of heart failure.

Assessment of sleep is traditionally performed in a polysomnographic sleep study at a dedicated sleep facility. Polysomnographic studies involve acquiring sleep-related data, including the patient's typical sleep patterns and the physiological, environmental, contextual, emotional, and other conditions affecting the patient during sleep. However, such studies are costly, inconvenient to the patient, and may not accurately represent the patient's typical sleep behavior.

Sleep assessment in a laboratory setting presents a number of obstacles in acquiring an accurate picture of a patient's typical sleep patterns including arousals and sleep disorders. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Among the various parameters for assessing sleep disordered breathing (SDB), the pattern of apnea, for example, yields important information as well as an apnea-hypopnea index (AHI) and/or oxygen desaturation indication. For cardiovascular consequences due to severe apnea, this pattern information may be more relevant than the AHI value itself. Periodicity of disordered breathing represents a pattern that, when discerned in a manner consistent with the principles of the present invention, can be useful for detecting apnea/hypopnea events, computing an AHI value, discriminating between types of disordered breathing, and determining the severity of a patient's heart failure status.

Determining the severity of a patient's heart fail status based on periodic disordered breathing (PDB) may involve, for example, determining presence of the PDB in each of several physiological states, including sleep, wakefulness without exercise, and wakefulness with exercise. Detection of periodic disordered breathing during such physiological states can be an indication of the relative severity of the patient's heart failure condition. For example, detection of periodic disordered breathing only during sleep is of concern. Detection of periodic disordered breathing during both sleep and exercise is of greater concern. Detection of periodic disordered breathing during sleep, exercise, and wakefulness without exercise is of greatest concern, in particular within the context of heart failure. In this context, detecting the presence of periodic breathing relative to patient state (e.g., physiological state) is a prognostic marker for heart failure severity. For example, detecting the present of periodic breathing during the day and in the absence of patient exercise is indicative of a severely compromised patient condition, particular in heart failure patients.

Severity of a patient's periodic disordered breathing can also be assessed by determining the percentage of time (i.e., burden) the patient is experiencing periodic disordered breathing. Severity may also be determined by discriminating the type of periodic disordered breathing. For example, the envelope of the respiration-modulated signal may be analyzed to discriminate between obstructive sleep apnea (OSA), central sleep apnea (CSA), and mix of OSA and CSA. Envelope amplitude and duration of envelope fluctuation may be evaluated for discriminating between OSA and CSA, such as in the manner described in U.S. Pat. No. 6,856,829, which is hereby incorporated herein by reference. Severity of a patient's periodic disordered breathing may also be determined by determining a depth of a change in peaks of the envelope or the frequency of envelope modulation.

Embodiments of the present invention are directed to methods and systems for detecting the presence of periodic disordered breathing, such as apnea, hypopnea, and Cheyne-Stokes respiration, among others. Embodiments of the present invention employ an implantable or partially implantable device or sensor that is implemented to sense a respiration-modulated signal of the patient. As is shown in FIG. 1, a signal representative of patient respiration is developed 102 by use of such a device or sensor. This signal is processed such that an envelope of the signal is provided 104. The signal envelope is analyzed to detect periodicity 106, if any. Presence or absence of periodic disordered breathing is determined 108 based on the periodicity of the envelope.

According to one approach, a raw signal of block 102 in FIG. 1 is removed from its trend and rectified to produce an envelope of the raw signal. The envelope may also be generated by performing peak detection of the raw signal or down-sampling the signal. The envelope, rather than the raw signal itself, is preferably used in the analysis to determine presence or absence of periodic disordered breathing. The envelope may be provided using analog or, more preferably, digital signal processing. The envelope may also be provided using an algorithmic approach as is known in the art.

In this envelope signal, only periodic disordered breathing will exhibit a periodic pattern, while various forms of non-periodic breathing, such as normal respiration during rest or exercise, single apnea events or noise, will have either a random pattern or, theoretically, a flat envelope. Detection of envelope periodicity may thus be used to determine the presence or absence of periodic disordered breathing, such as various forms of apnea. Detecting periodic disordered breathing according to the present invention can be made robust against "respiratory noise" (i.e., normal breathing or electrical noise).

Further analysis of the signal envelope may reveal other aspects of a patient's periodic disordered breathing. For example, the total duration of the detected periodic portions of the signal envelope having a frequency range below normal respiration frequency can be used to estimate the patient's AHI. Also, the frequency of the periodicity and the stability of the detected periodic disordered breathing may also be provided as measures for periodic disordered breathing severity. According to various approaches, once a periodic region of the signal envelope has been identified, respiration signal morphology and/or timings can be applied to further differentiate whether the periodic disordered breathing is obstructive, central or hypopnea in type.

Embodiments of the present invention may use any of a number of different physiological signals that are modulated by patient respiration. Suitable signals include respiratory-modulated cardiac electrical signals and respiratory-modulated mechanical signals. By way of example, suitable signals include ECG signals (surface, intrathoracic, or subcutaneous non-intrathoracic), R-R intervals (e.g., peak R modulation), P-R intervals, other conduction intervals, QRS vector shifts as a function of respiration, systolic time interval (STI), pulse transit time (PTT), blood pressure, intrathoracic pressure, plural pressure, left ventricular transmural pressure, transthoracic impedance, intra-cardiac pressures, minute ventilation, pulse okimetery signals, plethysmography signals, signals indicative of diaphragmatic movement, heart movement or acceleration due to lung movement, heart sounds, among other physiological signals that may be used as a surrogate for respiration.

Figure 2:
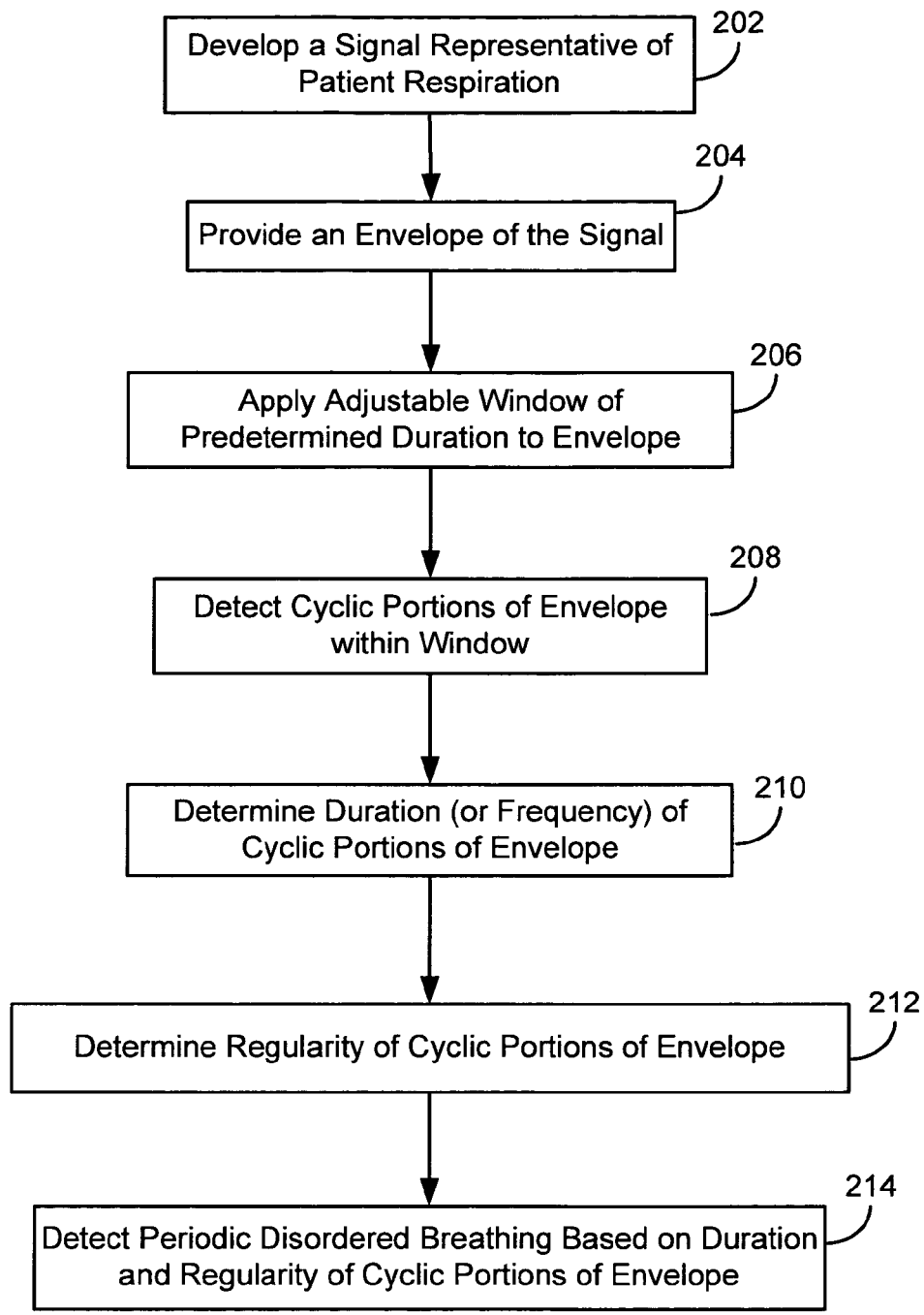
FIG. 2 illustrates a method for detecting the presence of periodic disordered breathing in accordance with embodiments of the present invention.

Turning now to FIG. 2, there is shown various processes for detecting a patient's periodic disordered breathing according to embodiments of the present invention. A signal representative of patient respiration is developed 202, from which an envelope of the signal is provided 204. An adjustable window having a predetermined duration is applied 206 to the envelope. Cyclic portions of the envelope falling within the window are detected 208, if present.

A duration or frequency of the cyclic portions of the envelope is determined 210. Regularity of the cyclic portions of the envelope is determined 212. Periodic disordered breathing is detected 214 based on the duration and regularity of the cyclic portions of the envelope. Evaluating regularity of the patient's disordered breathing facilitates the determination of whether or not the disordered breathing is periodic within the context of the adjustable window. Evaluating the duration or frequency of the cyclic portions facilitates the determination of whether or not the patient's respiration is characterizable as disordered breathing, such as sleep apnea.

Figure 3:
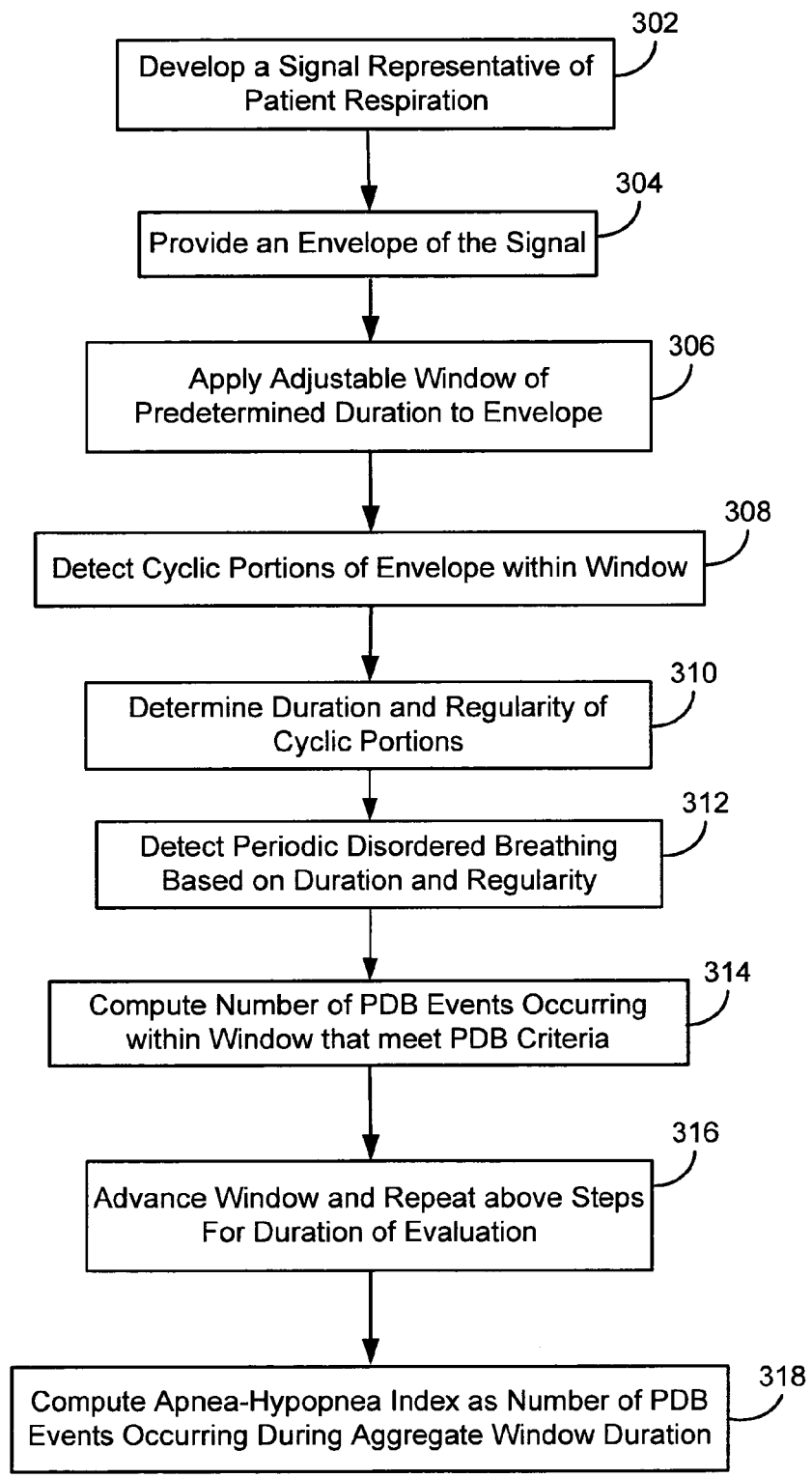
FIG. 3 illustrates a method for detecting the presence of periodic disordered breathing and computing an estimate of the patient's apnea-hypopnea index in accordance with embodiments of the present invention.

FIG. 3 shows various processes for detecting periodic disordered breathing of a patient according to further embodiments of the present invention. As in the previous figure, a signal representative of patient respiration is developed 302, from which an envelope of the signal is provided 304. An adjustable window having a predetermined duration is applied 306 to the envelope, and cyclic portions of the envelope falling within the window are detected 308, if present. A duration/frequency and regularity of the cyclic portions of the envelope are determined 310. Periodic disordered breathing is detected 312 based on the duration and regularity of the cyclic portions of the envelope.

The number of periodic disordered breathing events occurring within the window that meet predetermined criteria is computed 314. The window is advanced 316 and processes 302-314 are repeated 316, thus producing a number of periodic disordered breathing events occurring within each of a number of windows. The patient's estimated AHI is computed 318 based on the total number of PDB events occurring during the aggregate window duration.

According to one approach, a patient's AHI may be estimated using a respiration-modulated signal envelope based on the following equation:

$$\frac{TotalApneaDuration(m) \cdot 60}{TST(H) \cdot regularity_{MEAN}(s)} \qquad [1]$$

wherein, Total Apnea Duration is measured in minutes, TST represents the total duration of patient testing/evaluation measured in hours, and the regularity$_{MEAN}$ is measured in seconds and represents the mean duration of an apnea event, such as about 50 seconds.

Figure 4:
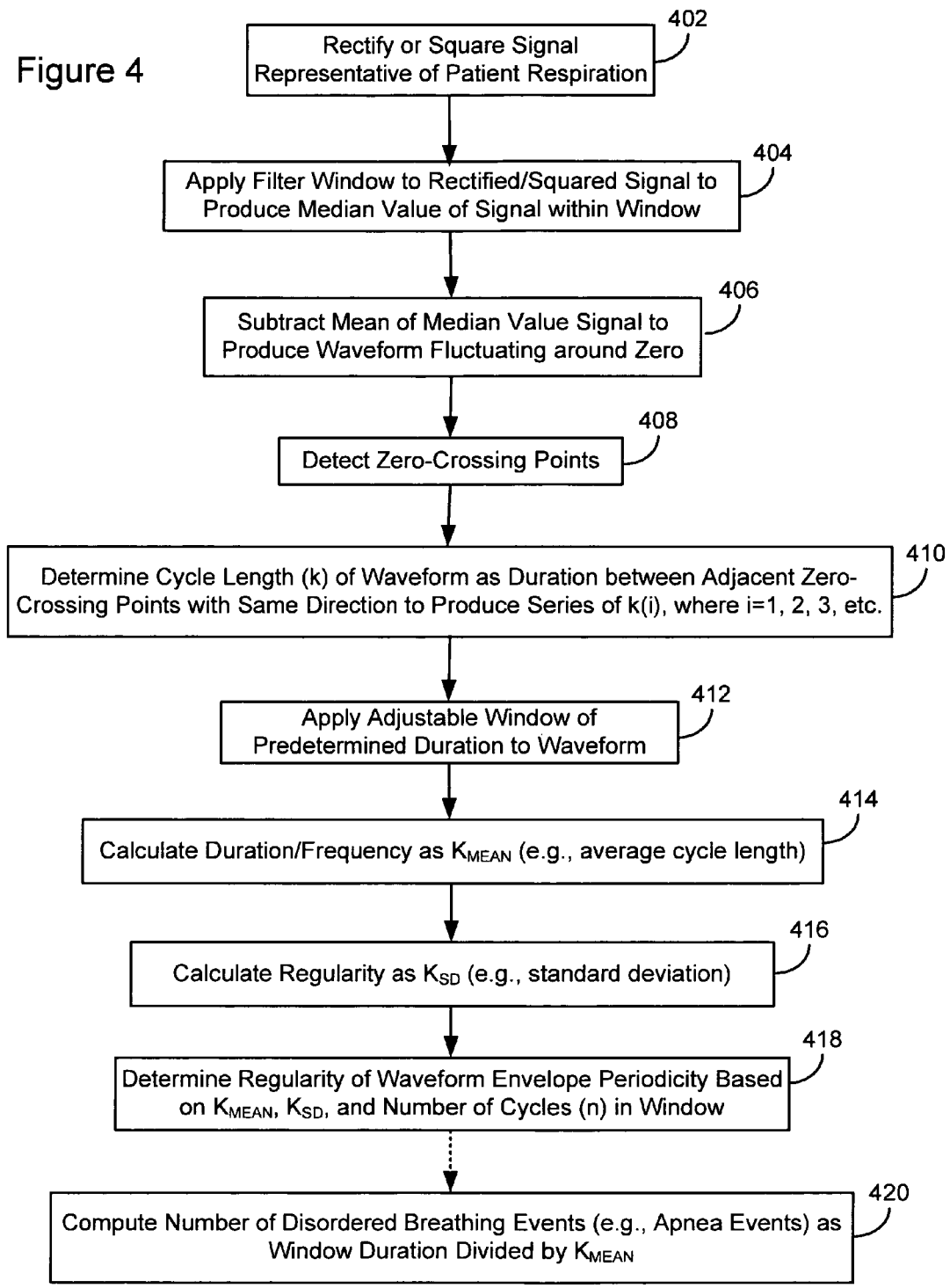
FIG. 4 illustrates a method for detecting the presence of periodic disordered breathing and computing the number of apnea events occurring within a predefined time period in accordance with embodiments of the present invention.
Figure 6A:
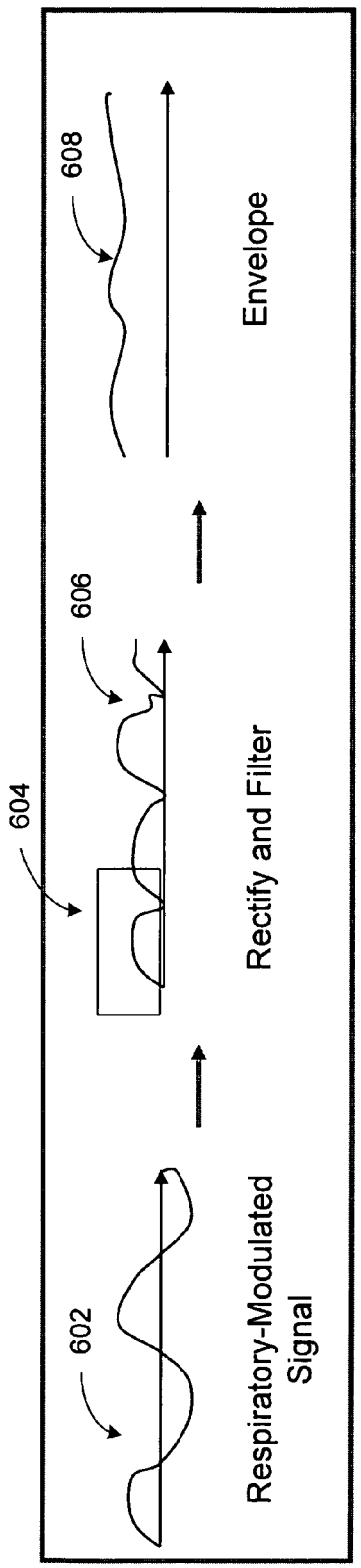
FIG. 6A illustrates the development of a signal envelope via rectification and filtering of a respiratory-modulated signal in accordance with embodiments of the present invention.

FIG. 4 shows various processes for detecting periodic disordered breathing of a patient according to other embodiments of the present invention. According to the embodiment of FIG. 4, and with reference to FIG. 6A, a signal representative of patient respiration 602, such as a trans-thoracic impedance signal (e.g., minute ventilation signal), is rectified 402. The signal may be rectified using full wave rectification. The signal may alternatively be squared and low pass filtered.

Figure 6C:
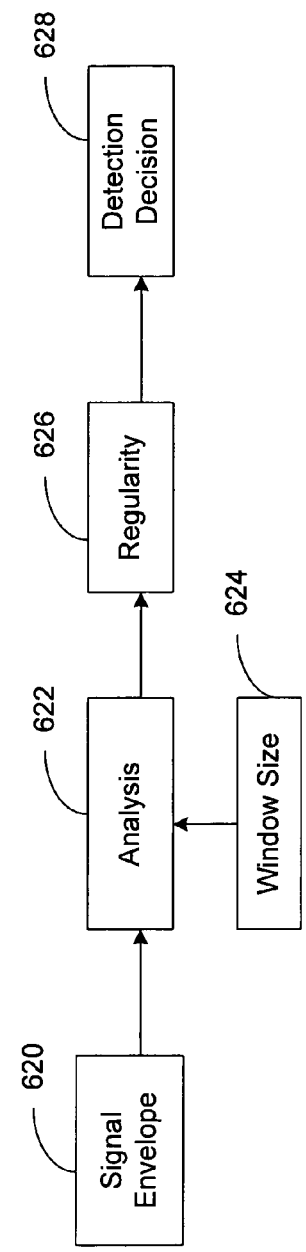
FIG. 6C illustrates various processes of a periodic disordered breathing detection methodology in accordance with embodiments of the present invention.
Figure 6B:
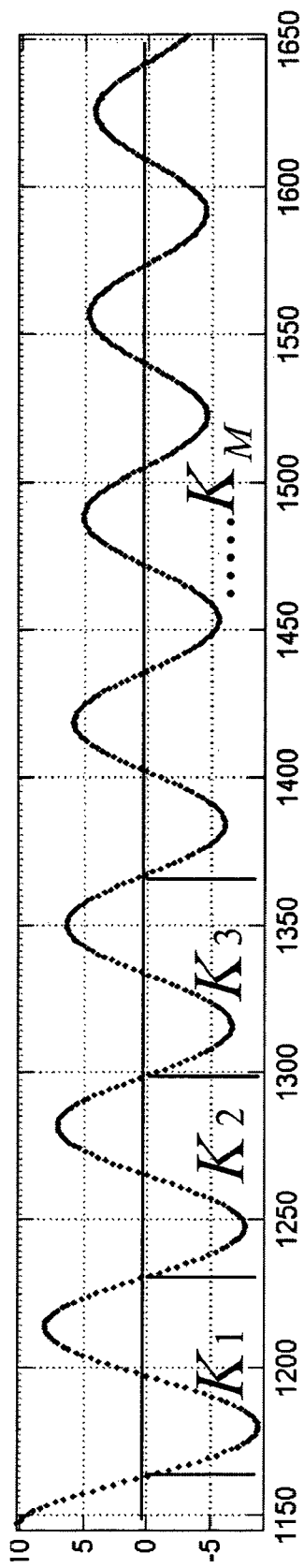
FIG. 6B illustrates a signal envelope from which periodicity attributes are derived via analyses in accordance with embodiments of the present invention.

A filter window 604 of predetermined duration (e.g., 5 seconds) is applied 404 to the rectified/squared signal 606 to produce a median value of the signal 608 within the filter window 604. The mean of the median value signal is subtracted 406 to produce a waveform (e.g., envelope) that fluctuates around zero or DC, such as that shown in FIG. 6B. FIG. 6C is a generalized showing of processes that are implemented on the waveform, including analysis 622 of the signal envelope 620 within a window 624 of predetermined size, determination of regularity, of periodic portions of the envelope, and deciding 628 whether or not periodic disordered breathing (e.g., apnea) has been detected.

Returning to FIG. 4, the zero-crossing points of the waveform (e.g., envelope) are detected 408. As is discussed below, envelope periodicity may alternatively be determined using peak detection instead of zero-crossing detection. As is further shown in FIG. 6B, the cycle length (k) of the waveform is determined 410 as the duration between adjacent zero-crossing points with the same direction. This determination 410 results in the production of the series of k(i) cycles, where i=1, 2, 3, . . . M. An adjustable window of predetermined duration, such as 300 seconds, is applied 412 to the waveform. The duration (or frequency as the inverse of duration) is calculated 414 as the average cycle length, $K_{MEAN}$:

where $$K_{MEAN} = \frac{1}{M}\sum_{i=1}^{M} K_i \qquad [2]$$

The regularity of the k(i) cycles is calculated as the standard deviation, $K_{SD}$:

where $$K_{SD} = \sqrt{\frac{\sum_{i=1}^{M}(K_i - K_{MEAN})^2}{M-1}} \qquad [3]$$

The regularity of waveform/envelope periodicity is determined 418 based on $K_{MEAN}$, $K_{SD}$, and the number of cycles, M, in the adjustable window. For example, when M>4 and if $K_{SD}$<3 seconds, then regularity is considered high. Then, if $K_{MEAN}$ is around 50 seconds, then this duration/frequency falls within the duration/frequency range of periodic disordered breathing, which typically ranges from about 0.02 Hz to about 0.1 Hz. A periodic pattern within the adjustable window can be determined with 100% confidence.

Periodic disordered breathing events, such as apnea events, can be estimated 420 by dividing the duration of the adjustable window by the value of $K_{MEAN}$. By way of example, for a 300 second adjustable window, the number of apnea events for this window is computed as 300 sec/$K_{MEAN}$.

It is noted that envelope periodicity may be determined using peak detection instead of zero-crossing detection, which is particularly useful for non-respiratory waveforms, such as ECG signals. For example, and with reference to FIG. 4, a change in slope from the negative to the positive peak of the signal envelope is representative of respiration may be detected, and this change would be indicative periodicity. Use of such a peak detection approach would eliminate the need for the processes depicted in boxes 404-408 in FIG. 4.

According to one peak detection approach, an ECG signal modulated by respiration is detected. Peak detection is performed on the QRS complex as the peak of the QRS complex is modulated by respiration. An envelope may be produced based on the detected peaks of the respiration-modulated QRS complexes in a known manner. Changes in the slope of this envelope can be detected, from which periodicity determinations may be made.

Figure 5:
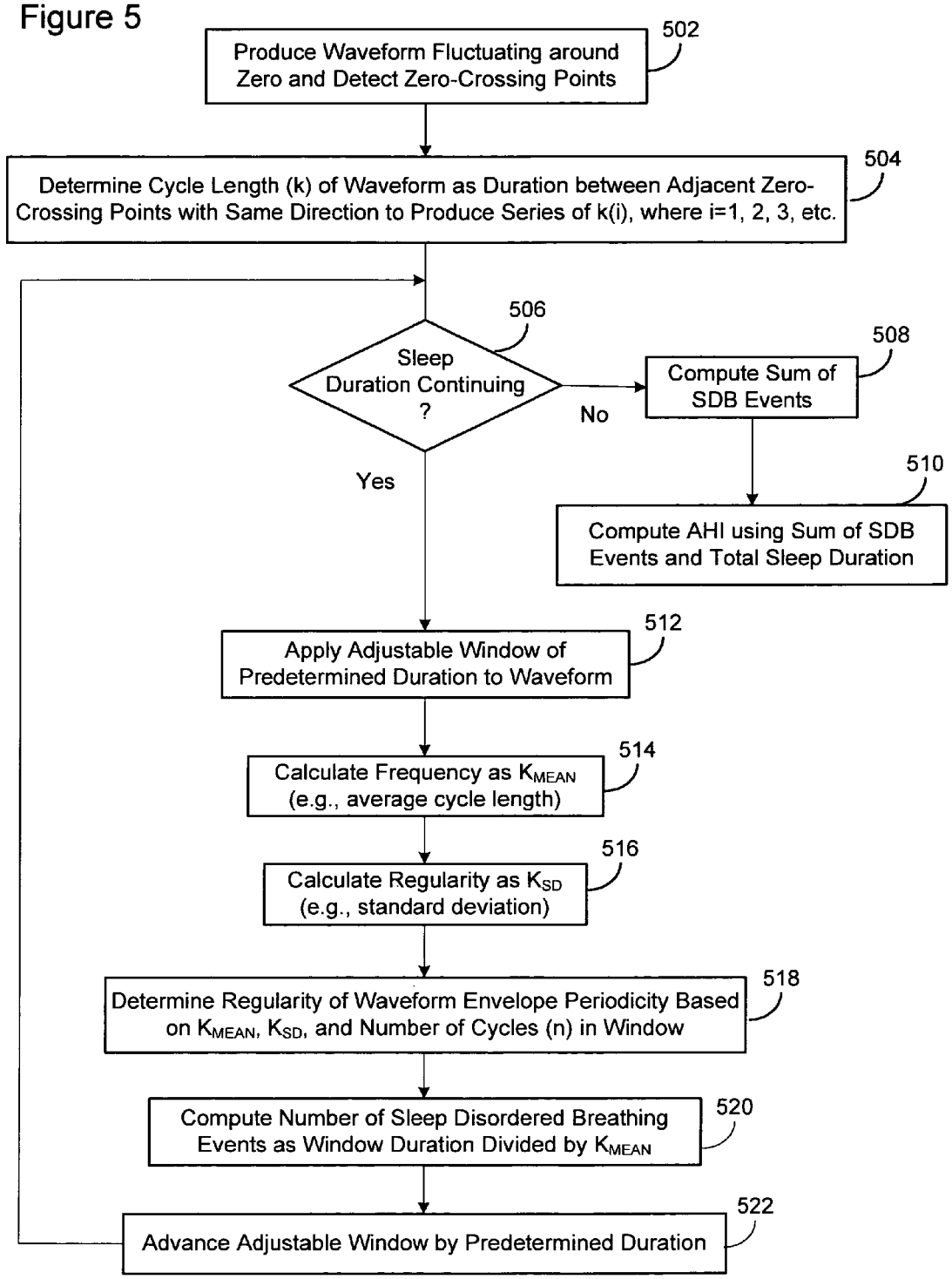
FIG. 5 illustrates a method for detecting the presence of periodic disordered breathing and computing an estimate of the patient's apnea-hypopnea index in accordance with embodiments of the present invention.

FIG. 5 shows various processes for computing a patient's estimated AHI in accordance with the principles of the present invention. In FIG. 5, it is assumed that the patient is asleep when the analysis is conducted. Confirmation that the patient is asleep can be accomplished in a number of ways, including use of an activity sensor, posture sensor, REM-modulated condition sensor, EEG sensor, or muscle atonia sensor, for example. Useful methods and devices for detecting sleep and sleep state are described in commonly owned U.S. Pat. No. 7,189,204 and U.S. Publication No. 2005/0043652, which are hereby incorporated herein by reference. It is noted that methodology for calculating AHI in accordance with the present invention is not limited to use during sleep, by may be used at anytime, including during the day (i.e., non-sleep times).

In a manner previously described with reference to FIG. 4, a waveform that fluctuates around zero is produced and zero-crossing points are determined 502. The cycle length (k) of the waveform is determined 504 as the duration between adjacent zero-crossing points with the same direction, thereby producing a series of k(i) cycles, where i=1, 2, 3, . . . M.

Processing continues for the duration 506 of patient sleep. An adjustable window of predetermined duration is applied 512 to the waveform. The duration/frequency and regularity are calculated 514, 516 in a manner previously described. Regularity of the envelope periodicity is determined and number of sleep disordered breathing events is computed 518 in a manner previously described. The adjustable window is advanced 522 by the predetermined duration, and processes 512-522 are repeated for the duration of patient sleep, expiration of a timer, occurrence of a predetermined event, or reception of a termination signal. After such terminating event, the sum of sleep disordered breathing events over the test duration is computed 508. The patient's estimated AHI can be computed using the sum of SDB events and total sleep duration as follows:

$$\frac{SumofSDBevents \cdot 60}{TotalSleepDuration(\min)} \quad [4]$$

FIGS. 7A-7F are waveforms that demonstrate the efficacy of the detection methodology of the present invention. FIG. 7A represents a raw respiratory-modulated signal obtained from a patient that is representative of normal breathing. In this case, the signal shown in FIG. 7A is a respiration signal, and FIG. 7B is a respiration signal representative of periodic disordered breathing.

FIG. 7C is the envelope of the signal shown in FIG. 7A developed in a manner described above. The signal envelope shown in FIG. 7C is predominately random in character, which is indicative of non-periodic breathing (i.e., normal breathing). FIG. 7D is the envelope of the signal shown in FIG. 7B developed in a manner described above.

FIGS. 7E-7F show calculated respiration envelopes for normal and periodic breathing based on peak detection of a trans-thoracic impedance signal. According to one peak detection approach, a trans-thoracic impedance signal (e.g., a minute ventilation or MV signal) is bandpassed filtered and subject to zero-cross/peak/valley detection to produce one peak point per breadth, which forms the envelope shown in FIG. 7E. Since apneas of periodic disordered breathing result in a lack of respiration, to maintain a reasonably stable sampling frequency (at ~0.3 Hz, the respiratory rate), zero tidal volume breaths can be added during apneic periods at a rate similar to the preceding section of normal respiration. This is shown in FIG. 7F.

The signal envelopes shown in FIGS. 7D and 7F exhibit periodicity, which is the characteristic pattern of periodic disordered breathing, such as apnea. As is discussed above, regularity and duration/frequency analyses performed on the signal envelopes of FIGS. 7D and 7F in accordance with the present invention can be used to determine if the waveform is indeed representative of periodic (i.e., regular) disordered breathing (i.e., of a duration/frequency consistent with apnea).

Figure 8:
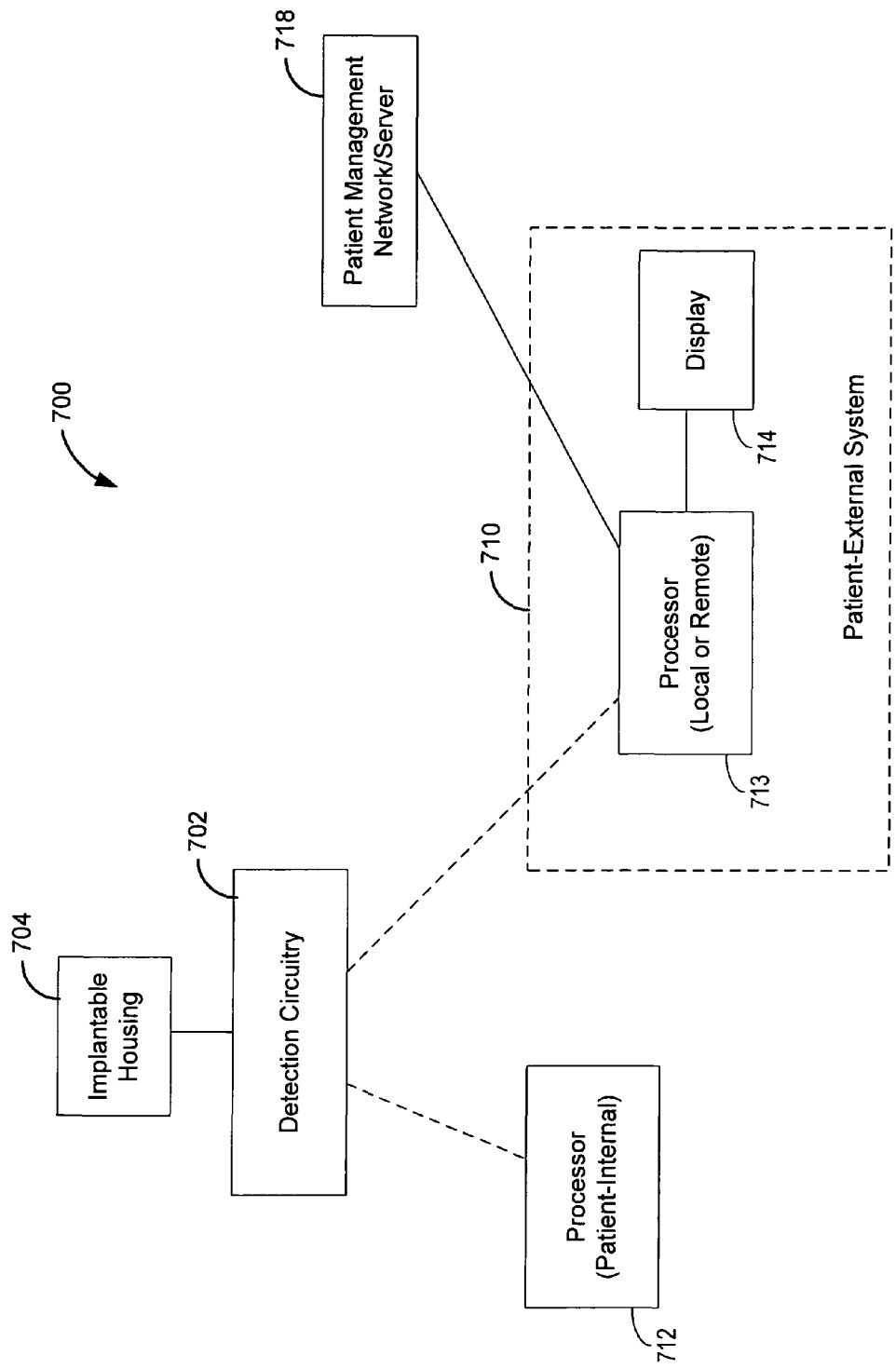
FIG. 8 is a block diagram of a diagnostic system configured to detect presence of periodic disordered breathing in accordance with embodiments of the present invention.

According to embodiments of the present invention, a disordered breathing diagnostic may be implemented with use of an implantable medical device or sensor. FIG. 8 is a block diagram of a diagnostic system 700 according to an embodiment of the present invention. According to the embodiment shown in FIG. 8, a disorder breathing diagnostic system 700 includes one or more implantable sensors disposed in a biocompatible enclosure or housing 704. The sensor is configured to sense a physiologic parameter useful in detecting patient respiration. Although described generally as being implantable, it is understood that all or some of the sensor/housing 704 may be patient-external in certain embodiments, such that the system 700 includes no patient-internal components. The sensor 704 is communicatively coupled to detection circuitry 702.

The detection circuitry 702 may be implantable or patient-external. For example, the detection circuitry 702 may be incorporated in a cardiac rhythm management or monitoring system that incorporates a disordered breathing diagnostic. A device that incorporates detection circuitry 702 may also be a nerve stimulation device or a positive airway pressure device, for example.

In one configuration, detection circuitry 702 may be disposed in implantable housing 704 and configured to simply detect patient respiration and telemeter respiration signals to a patient-external system 710 for further processing. In this embodiment, a processor 713 of the patient-external system 710 analyzes the respiration signal in a manner described herein. In a variant implementation, the respiration signal may be processed by a processor of a patient management network/server 718 (e.g., advanced patient management (APM) system) in a manner described herein. The results of the analyses performed by the patient-external system 710 and/or patient management network/sever 718 may be provided to a clinician (and/or the patient) via an output device, such as a display 714 (or an output device of the patient management network/sever 718). Features and functionality of a patient management network/server particularly well-suited for use in the context of the present invention are disclosed in U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In another configuration, the detection circuitry 702 and processor 712 are disposed in implantable housing 704. In this embodiment, processor 712 of the implantable system analyzes the respiration signal in a manner described herein. The processor 712 may determine the presence of periodic disordered breathing and telemeter data associated with such analyses to a patient-external system 710 (e.g., programmer, portable communicator, or bed-side system) and/or a patient management network/system 718.

The detection circuitry 702 may further be used in combination with therapy delivery circuitry configured to deliver therapy to treat a patient's disordered breathing. The sensor 704 may include one or more of transthoracic impedance sensors, EEG sensors, cardiac electrogram sensors, nerve activity sensors, accelerometers, posture sensors, proximity sensors, electrooculogram (EOG) sensors, photoplethysmography sensors, blood pressure sensors, peripheral arterial tonography sensors, and/or other sensors useful in sensing conditions associated with respiration, sleep, and breathing disorders.

As was briefly described above, detection circuitry 702 or processor 712 is configured to communicate with patient-external system 710, which may be a programmer, home/bed-side system, portable communicator or interface to a patient management network/sever 718, such as an advanced patient management system. The disordered breathing diagnostic system 700 shown in FIG. 8 may be implemented in a variety of implantable or patient-external devices and systems, including cardiac monitoring or energy delivery devices, nerve stimulation devices, and positive airway pressure devices, among others.

Figure 9:
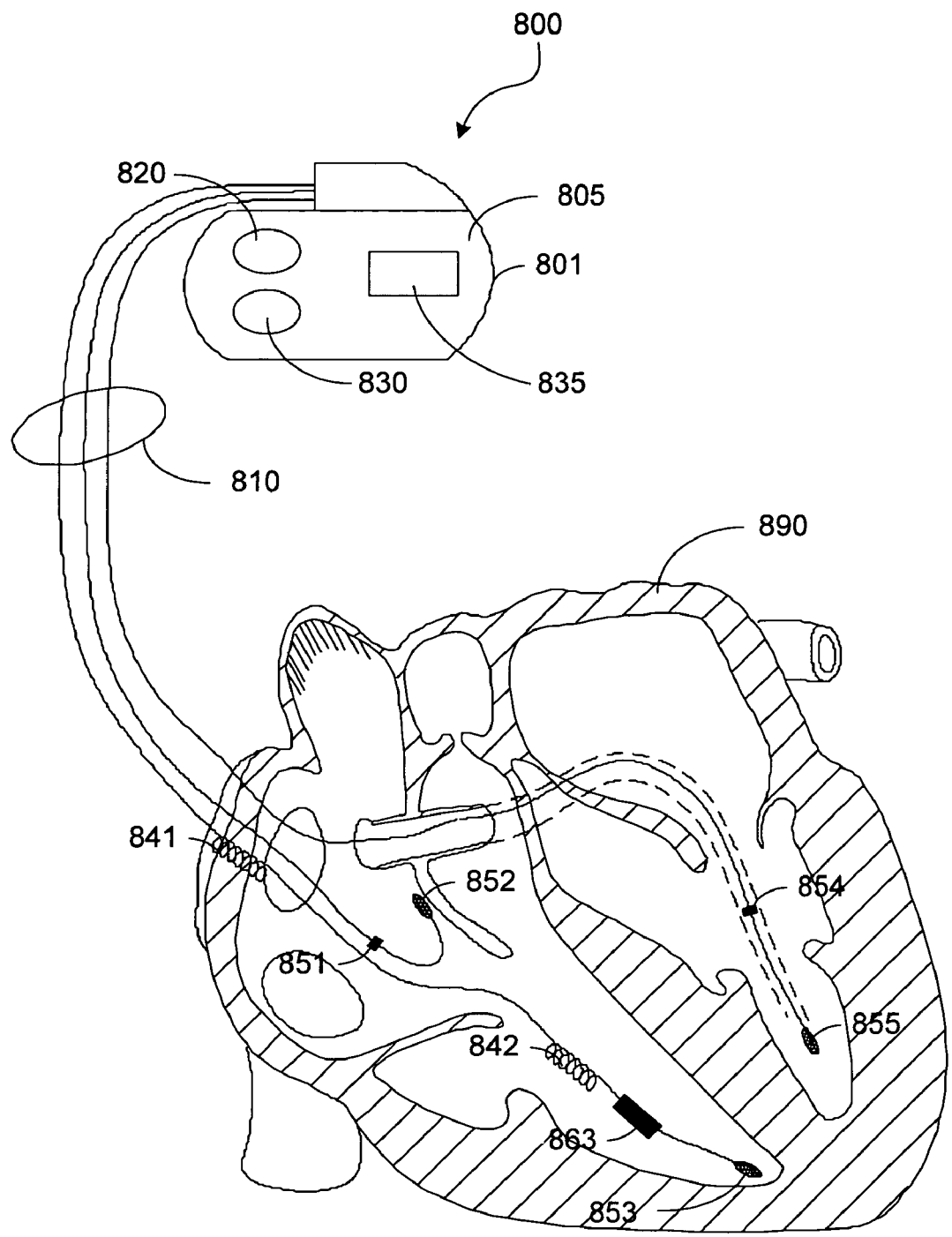
FIG. 9 is an illustration of a cardiac rhythm management system that implements periodic disordered breathing diagnostics in accordance with embodiments of the present invention.

FIG. 9 is an illustration of a cardiac rhythm management system that implements disordered breathing diagnostics in accordance with an embodiment of the present invention. The system 800 shown in FIG. 9 may be configured to include circuitry and functionality for periodic disordered breathing detection in accordance with embodiments of the invention. In this illustrative example, disordered breathing diagnostic circuitry 835 is configured as a component of a pulse generator 805 of a cardiac rhythm management device 800. The implantable pulse generator 805 is electrically and physically coupled to an intracardiac lead system 810. The disordered breathing diagnostic circuitry 835 may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 810 are shown inserted into the patient's heart 890. The intracardiac lead system 810 includes one or more electrodes configured to sense electrical cardiac activity of the heart, deliver electrical stimulation to the heart, sense the patient's transthoracic impedance, and/or sense other physiological parameters indicative of patient respiration. Portions of the housing 801 of the pulse generator 805 may optionally serve as a can electrode.

Communications circuitry is disposed within the housing 801, facilitating communication between the pulse generator 805, which includes the disordered breathing diagnostic circuitry 835, and an external device, such as a sleep disordered breathing therapy device, programmer, and/or APM system. The communications circuitry can also facilitate unidirectional or bidirectional communication with one or more implanted, external, cutaneous, or subcutaneous physiologic or non-physiologic sensors, patient-input devices and/or information systems.

The pulse generator 805 may optionally incorporate an activity sensor 820 disposed in or on the housing 801 of the pulse generator 805. The activity sensor 820 may be configured to sense patient motion and/or posture for purposes of determining the physiological state of the patient, such as whether the patient is sleeping, awake but not exerting/exercising, or awake and exerting/exercising. In one configuration, the activity sensor 820 may include an accelerometer positioned in or on the housing 801 of the pulse generator 805. If the activity sensor 820 incorporates an accelerometer, the accelerometer may also provide acoustic information, e.g. rales, coughing, S1-S4 heart sounds, cardiac murmurs, and other acoustic information.

The lead system 810 of the CRM device 800 may incorporate a transthoracic impedance sensor that may be used to acquire the patient's cardiac output or other physiological conditions related to the patient's sleep disorder(s). The transthoracic impedance sensor may include, for example, one or more intracardiac electrodes 840, 842, 851-855, 863 positioned in one or more chambers of the heart 890. The intracardiac electrodes 841, 842, 851-855, 861, 863 may be coupled to impedance drive/sense circuitry 830 positioned within the housing of the pulse generator 805.

The impedance signal may also be used to detect the patient's respiration waveform and/or other physiological changes that produce a change in impedance, including pulmonary edema, heart size, cardiac pump function, etc. The respiratory and/or pacemaker therapy may be altered on the basis of the patient's heart condition as sensed by impedance.

In one implementation, the transthoracic impedance is used to detect the patient's respiratory waveform. A voltage signal developed at the impedance sense electrode 852 is proportional to the patient's transthoracic impedance and represents the patient's respiration waveform. The transthoracic impedance increases during respiratory inspiration and decreases during respiratory expiration. The transthoracic impedance may be used to determine the amount of air moved in one breath, denoted the tidal volume and/or the amount of air moved per minute, denoted the minute ventilation.

The lead system 810 may include one or more cardiac pace/sense electrodes 851-855 positioned in, on, or about one or more heart chambers for sensing electrical signals from the patient's heart 890 and/or delivering pacing pulses to the heart 890. The intracardiac sense/pace electrodes 851-855, such as those illustrated in FIG. 8, may be used to sense and/or pace one or more chambers of the heart, including the left ventricle, the right ventricle, the left atrium and/or the right atrium. The lead system 810 may include one or more defibrillation electrodes 841, 842 for delivering defibrillation/cardioversion shocks to the heart.

The pulse generator 805 may include circuitry for detecting cardiac arrhythmias and/or for controlling pacing or defibrillation therapy in the form of electrical stimulation pulses or shocks delivered to the heart through the lead system 8 10. Disordered breathing diagnostic circuitry 835 may be housed within the housing 801 of the pulse generator 805. The disordered breathing diagnostic circuitry 835 may be coupled to various sensors, including the transthoracic impedance sensor 830, activity sensor 820, EEG sensors, cardiac electrogram sensors, nerve activity sensors, and/or other sensors capable of sensing physiological signals useful for sleep disorder detection.

Detection methods and systems of the present invention may be used for diagnostic purposes and/or to alert a patient or a clinician that periodic disordered breathing is present. Alternatively or additionally, the detection methods and systems may be used to form sleep disorder therapy decisions, such as by, allowing clinicians to modify or initiate sleep disorder treatment in order to mitigate detected sleep disorders. Further, the detection of periodic disordered breathing may also be used to automatically initiate disordered breathing therapy to prevent or mitigate a sleep disorder. Also, detection and measurement of periodic breathing severity in accordance with the principles of the present invention may be used to measure heart failure status, such as in the manners disclosed in commonly owned U.S. Pat. No. 7,766,840, which is hereby incorporated herein by reference.

Various modifications and additions may be made to the embodiments discussed herein without departing from the scope of the present invention. In some configurations, for example, implantable or partially implantable devices that sense patient respiration and determine presence of periodic disordered breathing may be used in combination with a patient-implantable medical device or a patient-external medical device. In other configurations, patient-external devices that sense patient respiration and determine presence of periodic disordered breathing may be used in combination with a patient-implantable medical device or a patient-external medical device. A wide variety of sensor and medical device configurations that provide for the development and analysis of periodic disordered breathing data are contemplated. Accordingly, the scope of the present invention should not be limited by the particular embodiments described above, but should be defined only by the claims set forth below and equivalents thereof.

The invention claimed is:

1. A method, comprising:
  developing, patient internally, a signal representative of patient respiration;
  providing an envelope of the signal;
  detecting periodicity of the envelope; and
  determining presence of periodic disordered breathing based on the periodicity of the envelope by computing a parameter characterizing envelope cycle length for multiple envelope cycles occurring within a time window, the parameter comprising one or both of a standard deviation ($K_{SD}$) of duration for n envelope cycles and a duration of the time window divided by a mean ($K_{MEAN}$) indicative of average envelope cycle length, wherein developing, detecting, and determining are performed at least in part by circuitry, and wherein n is a number.

2. The method of claim 1, wherein providing the envelope of the signal comprises squaring and low pass filtering the signal.

3. The method of claim 1, wherein providing the envelope of the signal comprises performing peak detection on the signal or downsampling the signal.

4. The method of claim 1, wherein detecting periodicity of the envelope comprises determining regularity of envelope periodicity.

5. The method of claim 1, wherein the parameter comprises the standard deviation ($K_{SD}$) parameter and the envelope periodicity is determined based on the standard deviation ($K_{SD}$) being less than a first threshold and n being greater than a second threshold.

6. The method of claim 1, wherein determining the presence of periodic disordered breathing comprises determining regularity of envelope periodicity and a duration of envelope cycles occurring within the time window of predetermined duration.

7. The method of claim 1, wherein determining the presence of periodic disordered breathing comprises computing, within the time window of predetermined duration, the mean ($K_{MEAN}$) indicative of average envelope cycle length and the standard deviation ($K_{SD}$) of the mean ($K_{MEAN}$) computed for n envelope cycles occurring within the time window.

8. The method of claim 7, wherein the presence of periodic disordered breathing is determined if the standard deviation ($K_{SD}$) is less than a first threshold, n is greater than a second threshold, and $K_{MEAN}$ falls within a third threshold range.

9. The method of claim 1, wherein the parameter comprises the duration parameter of the time window, the time window is of a predetermined duration, and the method further comprises computing a number of periodic disordered breathing events occurring within the time window of predetermined duration by dividing the predetermined duration by the mean ($K_{MEAN}$) indicative of average envelope cycle length.

10. The method of claim 9, further comprising computing an estimated apnea-hypopnea index based on the number of periodic disordered breathing events occurring within each of a plurality of the time windows, a total duration of the plurality of time windows defining a duration of patient sleep.

11. The method of claim 1, further comprising determining severity of the periodic disordered breathing.

12. The method of claim 11, wherein determining the severity of the periodic disordered breathing comprises distinguishing between central sleep apnea and obstructive sleep apnea.

13. The method of claim 11, wherein determining the severity of the periodic disordered breathing comprises determining the severity of a patient's heart failure condition by determining the presence of the periodic disordered breathing in each of a plurality of physiological states.

14. The method of claim 11, wherein determining the severity of the periodic disordered breathing comprises determining a frequency of the periodicity and a stability of the periodicity.

15. The method of claim 11, wherein determining the severity of the periodic disordered breathing comprises determining a depth of a change in peaks of the envelope.

16. The method of claim 1, wherein the signal representative of patient respiration comprises a respiratory-modulated physiological signal.

17. The method of claim 1, wherein each of providing, detecting, and determining is performed patient internally.

18. The method of claim 1, further comprising one or more of generating an alert, initiating a therapy, and changing delivery of the therapy in response to determination of presence of periodic disordered breathing.

19. A method, comprising:
developing a signal representative of patient respiration;
providing an envelope of the signal;
determining periodicity of the envelope; and
determining presence of periodic disordered breathing based on the periodicity of the envelope by computing a standard deviation ($K_{SD}$) of duration for n envelope cycles characterizing envelope cycle length for multiple envelope cycles occurring within a time window, wherein at least one of determining periodicity and determining presence is performed at least in part by circuitry, and wherein n is a number.

20. The method of claim 19, wherein developing, providing, determining periodicity, and determining presence are performed patient internally.

21. The method of claim 18, further comprising one or more of generating an alert, initiating a therapy, and changing delivery of the therapy in response to determination of presence of periodic disordered breathing.

22. A method, comprising:
developing a signal representative of patient respiration;
providing an envelope of the signal;
determining periodicity of the envelope; and
determining presence of periodic disordered breathing based on the periodicity of the envelope by computing a parameter characterizing envelope cycle length for multiple envelope cycles occurring within a time window, the parameter comprising the time window duration divided by a mean ($K_{MEAN}$) indicative of average envelope cycle length, wherein at least one of determining periodicity and determining presence is performed at least in part by circuitry.

23. The method of claim 22, wherein developing, providing, determining periodicity, and determining presence are performed patient internally.

24. The method of claim 22, further comprising one or more of generating an alert, initiating a therapy, and changing delivery of the therapy in response to determination of presence of periodic disordered breathing.

* * * * *

UNITED STATES PATENT AND TRADEMARK OFFICE
CERTIFICATE OF CORRECTION

| | | |
|---|---|---|
| PATENT NO. | : 7,819,816 B2 | Page 1 of 1 |
| APPLICATION NO. | : 11/392365 | |
| DATED | : October 26, 2010 | |
| INVENTOR(S) | : Pu et al. | |

It is certified that error appears in the above-identified patent and that said Letters Patent is hereby corrected as shown below:

<u>In the References Cited, U.S. Patent Documents:</u>

Page 2, Col. 1: "6,597,951 B2 7/2003 Kadhiresan et al." should read --6,597,951 B2 7/2003 Kramer et al.--.

Page 2, Col. 2: "6,741,885 B1 5/2004 Bornzin et al." should read --6,741,885 B1 5/2004 Park et al.--.

Page 2, Col. 2: "6,752,765 B1 6/2004 Strobel et al." should read --6,752,765 B1 6/2004 Jensen et al.--.

Col. 6, line 32: "pulse okimetery signals" should read --pulse oximetery signals--.

Signed and Sealed this
Eighteenth Day of January, 2011

David J. Kappos
*Director of the United States Patent and Trademark Office*